US010125771B2

(12) United States Patent
Caldwell et al.

(10) Patent No.: US 10,125,771 B2
(45) Date of Patent: Nov. 13, 2018

(54) COMPACT LIQUID NITROGEN PUMP

(71) Applicants: Shane A. Caldwell, Chicago, IL (US); Gang Li, Ontario (CA)

(72) Inventors: Shane A. Caldwell, Chicago, IL (US); Gang Li, Ontario (CA)

(73) Assignee: UCHICAGO ARGONNE, LLC, Chicago, IL (US)

( * ) Notice: Subject to any disclaimer, the term of this patent is extended or adjusted under 35 U.S.C. 154(b) by 895 days.

(21) Appl. No.: 14/476,443

(22) Filed: Sep. 3, 2014

(65) Prior Publication Data

US 2016/0061384 A1 Mar. 3, 2016

(51) Int. Cl.

| | |
|---|---|
| ***F17C 3/00*** | (2006.01) |
| ***F04D 29/00*** | (2006.01) |
| ***F04D 13/08*** | (2006.01) |
| ***A61B 18/02*** | (2006.01) |
| ***F04D 1/02*** | (2006.01) |
| ***F04D 3/02*** | (2006.01) |
| ***F04D 7/02*** | (2006.01) |
| ***F04D 9/00*** | (2006.01) |
| ***F04D 13/12*** | (2006.01) |

(52) U.S. Cl.

CPC ............... *F04D 1/025* (2013.01); *F04D 3/02* (2013.01); *F04D 7/02* (2013.01); *F04D 9/003* (2013.01); *F04D 13/08* (2013.01); *F04D 13/12* (2013.01); *F17C 2223/0161* (2013.01); *F17C 2227/0178* (2013.01)

(58) Field of Classification Search

CPC ...... F17C 2227/0135; F17C 2227/0178; F17C 3/00; F04D 29/2288; F04D 29/2277; F04D 13/083; A61B 18/02; A61B 18/0218

See application file for complete search history.

(56) References Cited

U.S. PATENT DOCUMENTS

| | | | | |
|---|---|---|---|---|
| 5,819,544 A * | 10/1998 | Andonian | F04B 15/08 | 62/50.2 |
| 6,059,535 A * | 5/2000 | Wichmann | F04D 13/08 | 415/56.1 |
| 6,230,516 B1 * | 5/2001 | Andonian | A62B 7/06 | 62/461 |
| 2011/0152849 A1 * | 6/2011 | Baust | A61B 18/02 | 606/21 |
| 2013/0183155 A1 * | 7/2013 | Stoicescu | F04D 29/2277 | 416/175 |
| 2013/0263608 A1 * | 10/2013 | Thornton-Wood | F25D 3/102 | 62/49.1 |

* cited by examiner

*Primary Examiner* — Frantz Jules
*Assistant Examiner* — Erik Mendoza-Wilkenfe
(74) *Attorney, Agent, or Firm* — Cherskov Flaynik & Gurda, LLC

(57) ABSTRACT

The invention provides a cryogenic liquid pump system, having a first end with at least an insulating lid and motor; a second end, wherein the second end is a pump, said pump comprising an impeller; and a gas release plate upstream of the impeller; and a shaft disposed between the first end and the second end, wherein the motor imparts mechanical energy to the pump through the shaft. Also provided is a method for preventing cavitation of a cryogenic liquid in a cryogenic pump, the method having the steps of constantly maintaining pressure on the liquid in the pump and evacuating gas bubbles that form within the pump.

17 Claims, 15 Drawing Sheets

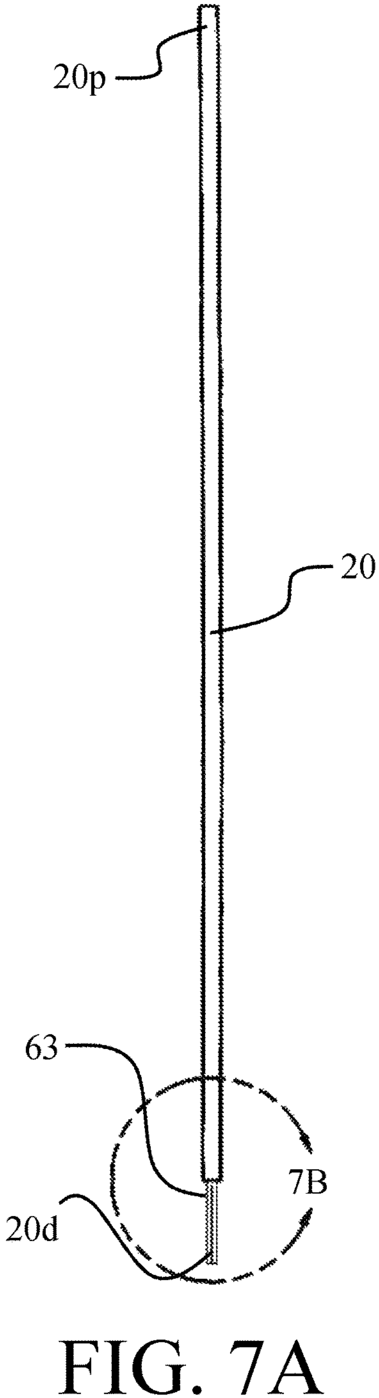
FIG. 7A
FIG. 7B
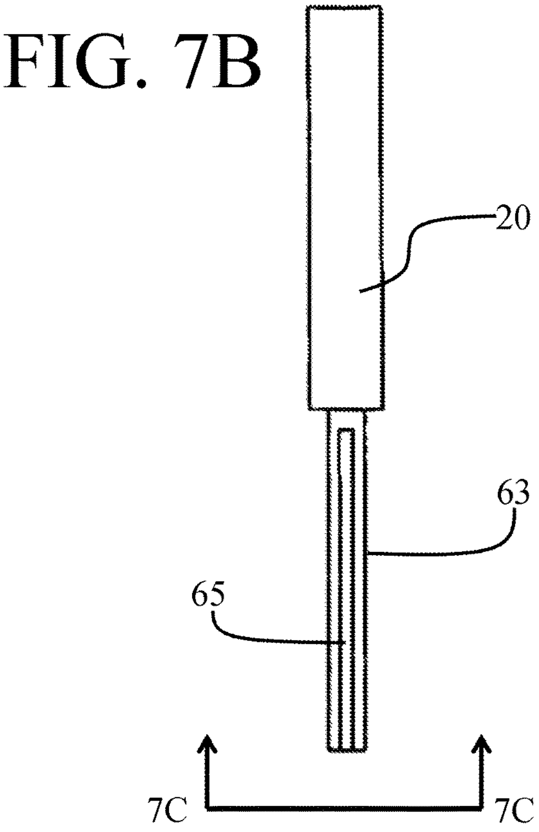
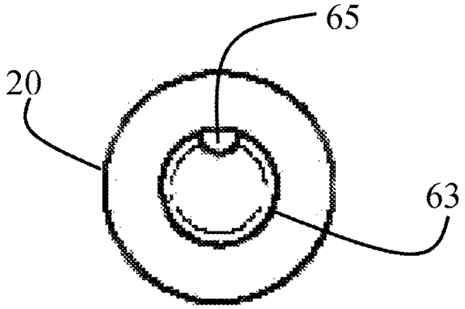
FIG. 7C

COMPACT LIQUID NITROGEN PUMP

CONTRACTUAL ORIGIN OF THE INVENTION

The U.S. Government has rights in this invention pursuant to Contract No. DE-AC02-06H11357 between the U.S. Department of Energy and UChicago Argonne, LLC, representing Argonne National Laboratory.

BACKGROUND OF THE INVENTION

1. Field of the Invention

The invention relates to a cryogenic fluid pump that is capable of continuously recirculating a cryogenic fluid for several weeks without user intervention.

2. Background of the Invention

Liquid nitrogen and other cryogenic liquids are used in a variety of scientific applications to cool experimental systems. For instance, cryogenic liquids provide favorable kinetics, confer improved vacuum conditions, and reduce the amount of contaminants in experimental procedures.

Some experiments require a constant flow of a liquid cryogenic at a low rate. A "low rate" is generally considered to be a rate less than 10 L/min. Many currently available cryogenic pumps are unsuitable for continuous operation at this rate. Further, not all pumps can be adapted to operate at a flow rate lower than their designed flow rate. Centrifugal pumps in particular are not designed to operate at rates much higher or lower than their manufacturer's stated best efficiency flow rate. Therefore, providing a steady stream of cryogenic liquid to some experiments is a challenge.

One example in which this cryogenic pumping challenge is particularly acute is ion-trapping experiments, such as Paul Traps. In Paul Traps, buffer gases are used to aid in ion transport and confinement. Bringing the buffer gas from room temperature to the temperature of a cryogenic liquid significantly reduces the spatial spread of trapped ions and improves the gas purity in the cooling region. These improvements increase the trap storage times. Longer trap storage times would allow for more accurate observation of the trapped ion. In some instances, meaningful observation can take days or weeks, but providing the small, constant flow of cryogenic liquid required for these long-term experiments has proven difficult.

Typically, the cryogenic liquid is continuously pumped by self-pressurization into the experimental setup and then lost downstream. Self-pressurization pumps use the increasing gas pressure caused by the boiling liquid inside the sealed Dewar container to push the liquid downstream. The pressure gradient driving the flow is lost in conventional methods during attempts to re-collect the liquid. Recirculation requires liquid to flow both into and out from the reservoir, but self-pressurization pumps can only support outward flow. Since the cryogenic liquid cannot be recovered, a very large supply of cryogenic liquid is required for the duration of the experiment. Obtaining and maintaining such a large supply of cryogenic liquid can be difficult, especially in small laboratory setups. Additionally, it also wastes material and effort.

Supplying the cryogenic liquid to the experimental device also provides its own difficulty. Because cryogenic liquids are boiling, they cannot be pulled through a circuit by a downstream pump. Instead, they must be driven by a positive-pressure device that is submerged in the liquid. The types of positive-pressure devices that can withstand cryogenic temperatures are limited to centrifugal pumps inasmuch as such pumps do not contain flexible components that become brittle when exposed to extreme cold. However, centrifugal pumps are susceptible to cavitation, which is further exacerbated by the fact that cryogenic liquids are constantly boiling.

Cavitation occurs when vapor cavities, i.e., gas bubbles, form in a liquid as a result of forces acting on the liquid and subsequently collapse against the impeller vanes. One prominent reason for cavitation is the rapid change of pressure in the liquid, such as when a liquid experiences a steep pressure drop when it reaches the eye of the impeller in a pump. The pressure drop is caused by a decrease in flow area, which causes an increase in flow velocity. Cavitation in a pump causes large amounts of noise, vibration, pressure pulsation, degradation of pump components, and loss of efficiency. If the pump chamber is sufficiently filled with gas bubbles, the flow of liquid will cease entirely.

The problems of pump cavitation are further exacerbated if a continuous flow at a low rate is desired or if the flow resistance is high. Evaporation of the cryogenic liquid in the flow circuit creates high flow resistance. Therefore, a need exists in the art for a cryogenic liquid pump that is capable of providing continuous flow for a period of days, weeks, or months at a low flow rate without the attendant cavitation problems that beset other pumps.

State of the art liquid nitrogen pumps are commercially available. However, these pumps are large and extremely expensive. Further, they are unsuitable for cooling small laboratory equipment.

Thus, a further need exists in the art for a compact cryogenic pump that is relatively inexpensive and is suitable for small-scale laboratory experimentation. The pump should also supply cryogenic fluids at rates less than 10 L/min.

SUMMARY OF THE INVENTION

An object of the present invention is to address the deficiencies of state of the art liquid nitrogen pumps.

A further object of the present invention is to provide a cryogenic liquid pump that can operate continuously for days, weeks, or months. A feature of the present invention is that the pump contains a gas release plate. An advantage of the present invention is that the onset of cavitation is delayed because the gas bubbles in the pump's impeller are vented. Another feature of the present invention is that the pump impeller is fed by an inducer. An advantage of the present invention is that the inducer increases the local boiling point of the cryogenic liquid at the impeller by increasing the pressure on the cryogenic liquid, thereby preventing the formation of gas bubbles.

Another object of the present invention is to provide a cryogenic liquid pump that can cycle and recirculate a cryogenic liquid during a lengthy experimental procedure. A feature of the invention is that it provides a means for continuously refilling the Dewar container such that fluid pressures are maintained and do not drop within the pump. An advantage of the present invention is that a large store of cryogenic liquid is not necessary to maintain operation of the pump. A further advantage of the present invention is that small laboratories do not need to undertake the cost of building and maintaining large stores of cryogenic liquid. A still further advantage is that small laboratories do not need to devote a large portion of their supply of cryogenic liquids to a single experiment. Rather, the invented device and method can supply a plurality of systems requiring cryogenic fluid for extended periods of time, inasmuch as the capability for doing this is limited only by the fluid resistance of each circuit and the flow rates required by each system.

Still another object of the present invention is to provide a cryogenic liquid pump that can be used for small-scale laboratory experimentation. A feature of the present invention is that it is able to provide continuous flow at a low rate (approximately 2 L/min) while maintaining a pump head of two to three meters. An advantage of the present invention is that the pump is relatively small, powerful, and inexpensive compared to other state of the art cryogenic pumps.

Another object of the present invention is to provide a centrifugal pump that can operate over a relatively wide range of flow rates. A feature of the present invention is that it can operate at a flow rates between about 11 L/min and about 0.1 L/min by varying the voltage input to the motor. Another feature of the present invention is that the gas release plate allows the pump to operate at lower flow rates. Typically, when centrifugal pumps operate at a flow rate below their best efficiency point, the pumping power is converted to thermal energy because the liquid remains in the pump housing, and as a result, the temperature of the liquid in the pump housing will rise. An advantage of the present invention is that the cryogenic liquid in the Dewar container cools the liquid in the pump housing, and while some of the liquid will vaporize, the gas release plate removes the bubbles from the pump housing.

Yet another object of the present invention is to provide a cryogenic pumping system that can operate uninterrupted without technician intervention. A feature of one embodiment of the present invention is that the Dewar container storing the cryogenic liquid contains a level sensor. The level sensor triggers a valve on an exterior reservoir to replenish the Dewar container when the cryogenic liquid level falls below a certain point. An advantage of the present invention is that a technician does not need to constantly monitor the liquid level in the Dewar container to see if evaporation or leaks have reduced the liquid level to a point of insufficiency.

Briefly, the invention provides a cryogenic liquid pump system, said pump system comprising a first end having at least an insulating lid and motor; a second end, wherein the second end is a pump, said pump comprising an impeller; and a gas release plate upstream of the impeller; and a shaft disposed between the first end and the second end, wherein the motor imparts mechanical energy to the pump through the shaft.

Also provided is a method for preventing cavitation of a cryogenic liquid in a cryogenic pump, the method comprising constantly maintaining pressure on the liquid.

BRIEF DESCRIPTION OF THE DRAWINGS

The invention together with the above and other objects and advantages will be best understood from the following detailed description of the preferred embodiment of the invention shown in the accompanying drawings, wherein:

FIG. 7A shows the shaft of the present invention;

FIG. 7B is a detail view of the distal end of the shaft depicted in FIG. 7A;

FIG. 7C is a view of the bottom of the distal end of the shaft taken along line 7C-7C in FIG. 7B;

DETAILED DESCRIPTION OF THE INVENTION

The foregoing summary, as well as the following detailed description of certain embodiments of the present invention, will be better understood when read in conjunction with the appended drawings.

As used herein, an element step recited in the singular and preceded with the word "a" or "an" should be understood as not excluding plural said elements or steps, unless such exclusion is explicitly stated. Furthermore, the references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

The present invention is directed to a compact cryogenic pump. The pump is designed to work at rates less than 10 L/min, and as low as 0.1 L/min.

In Paul Trap experiments, the cryogenic pump has allowed for the establishment of longer trap times. As compared to previous methods, trap storage time were increased by several orders of magnitude from milliseconds to minutes or longer. The longer trap storage times made the observation of some previously unobservable ions possible. Trap times of two to five minutes were sufficient for the collection of data for all experiments run, but longer trap times are easily attainable.

Other experiments that can benefit from the small, constant flow of cryogenic liquids provided by the present invention include: (1) cooling of gas targets for heavy-ion reactions; (2) performing online experiments involving particle beams, such as experiments involving the Advanced Photon Source x-ray beam, the Argonne Tandem Linac Accelerator System, and other particle beams found in laboratories around the world; (3) operating certain semiconductor devices that only operate in cryogenic environments; (4) conducting superconductor research; and (5) studying the effects of cryogenic exposure on protein, cells, tissues, and other biologic material.

Figure 1A:
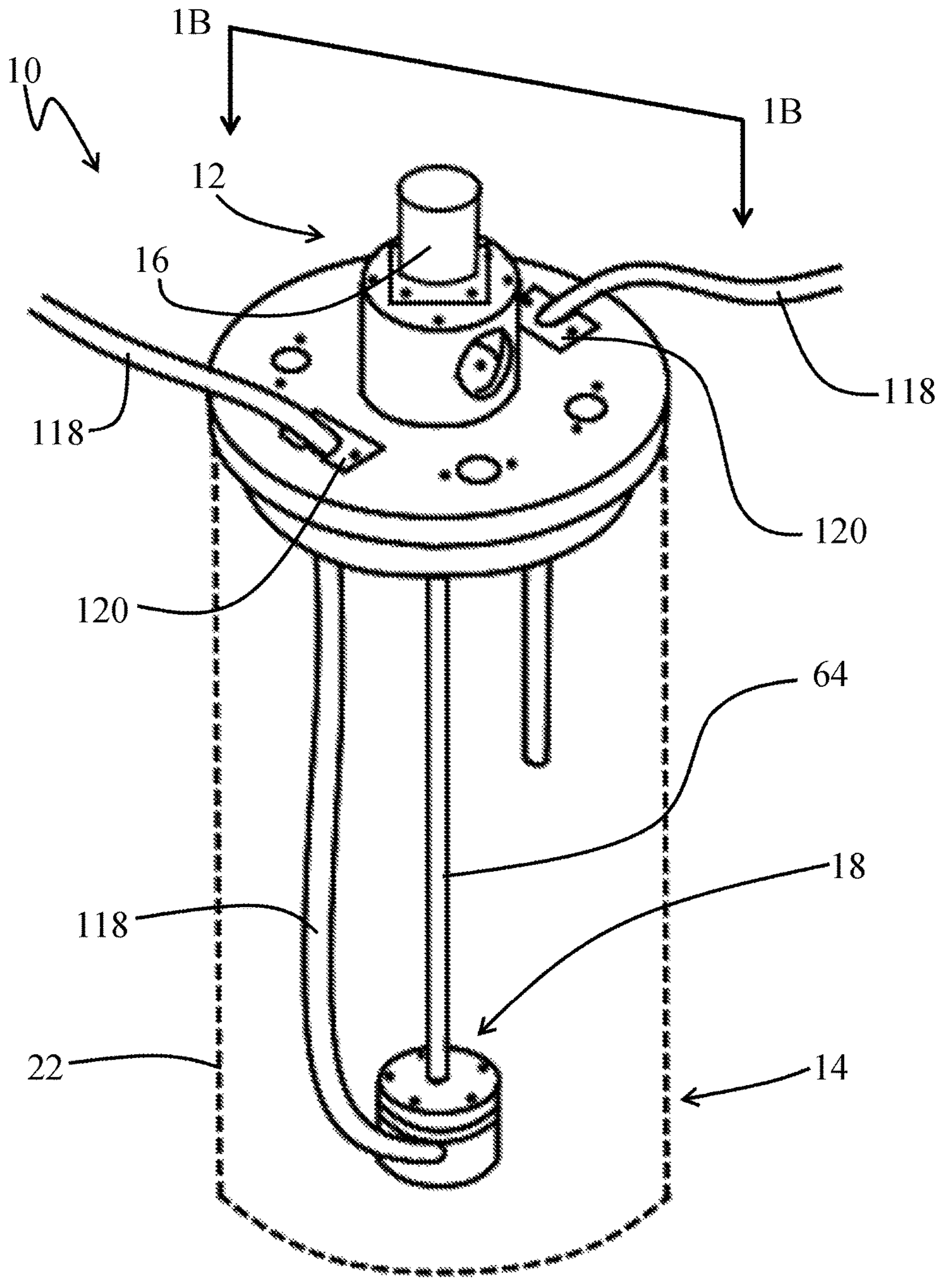
FIG. 1A is a perspective view of the cryogenic pump, in accordance with the features of the present invention.
Figure 1B:
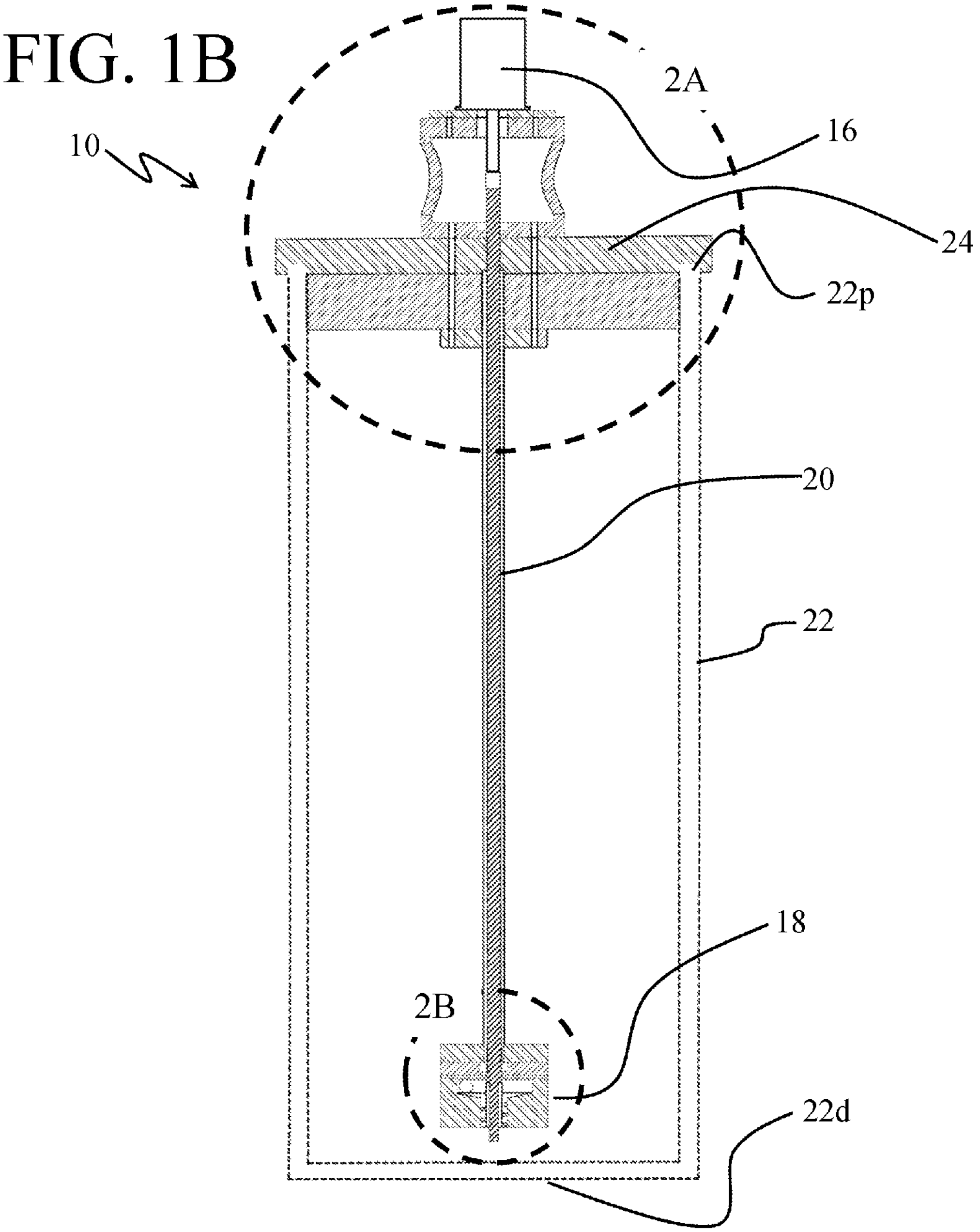
FIG. 1B is a sectional view taken along line 1B-1B in FIG. 1A.

As can be seen in FIGS. 1A-B, the device 10 has a first end 12 and a second end 14. Broadly, the device 10 features a motor 16 at the first end 12, a pump 18 at the second end 14, and a shaft 20 coaxially disposed with the longitudinal axis of the device so as to be positioned between the motor 16 and the pump 18 and so as to mechanically link the motor and the pump. In operation, the motor 16 drives rotation of the shaft 20 to create suction and discharge in the pump 18. The device 10 is substantially housed or otherwise encapsulated within a Dewar container 22 (depicted in phantom) such that the pump 18 draws cryogenic liquid from the Dewar container 22. The device 10 is designed to not only pump cryogenic liquid from the Dewar container 22 but also recirculate the cryogenic liquid through a system.

The Dewar container used in the present invention is a standard type Dewar container. Two different sizes were used in separate devices, to prove the concept. As such, the dimensions of the containers are merely illustrative and should not be construed as limiting the application of the device and method to other containers. For example, the first device had an outside diameter of about 10.38 inches, while the second device had an outside diameter of about 9.25 inches. Both Dewar containers were CF Series containers, manufactured by Cryofab, Inc. (Kenilworth, N.J.).

Motor/Lid Detail

The first end 12 of the device 10 not only contains the motor 16 to drive the pump 18, but it also contains a lid 24 (FIG. 1B) for the Dewar container 22. The lid defines a first surface 24*a* exposed substantially only to the environment outside of the Dewar container when attached to the container, and a second surface 24*b* exposed substantially only to the interior space of the container when the lid is attached to the Dewar container. As such, the Dewar container provides a means for preventing fluid communication between the pump 18 and the environment outside of the Dewar container.

As shown in FIG. 1B, the Dewar container 22 is in the upright position in which a closed distal end 22*d* is in contact with the ground or another support surface. An open proximal end 22*p* is vertically disposed of the distal end 22*d*. The second end 14 of the device 10 is inserted into the open proximal end 22*p* until the lid 24 contacts the proximal end 22*p* of the Dewar container 22. In an embodiment of the invention, the second end 14 of the device 10 does not contact the floor of the Dewar container 22. This vertical separation between the pump and the floor of the container provides a means for preventing detritus or other matter from being pulled into the pump. The bottom of the Dewar container 22 may be covered in ice or other solids, which should not be introduced into the pump 18. In this configuration, the device is substantially encapsulated by the Dewar container.

Alternatively, the lid 24 rests substantially flat on the lip defining the open proximal end 22*p* of the Dewar container 22.

Figure 3A:
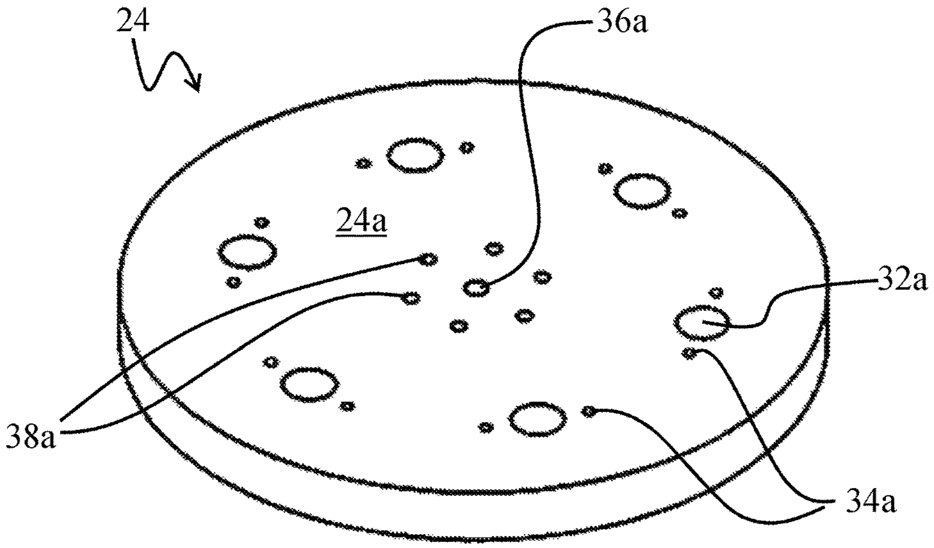
FIG. 3A is a depiction of the top surface of the lid.
Figure 3B:
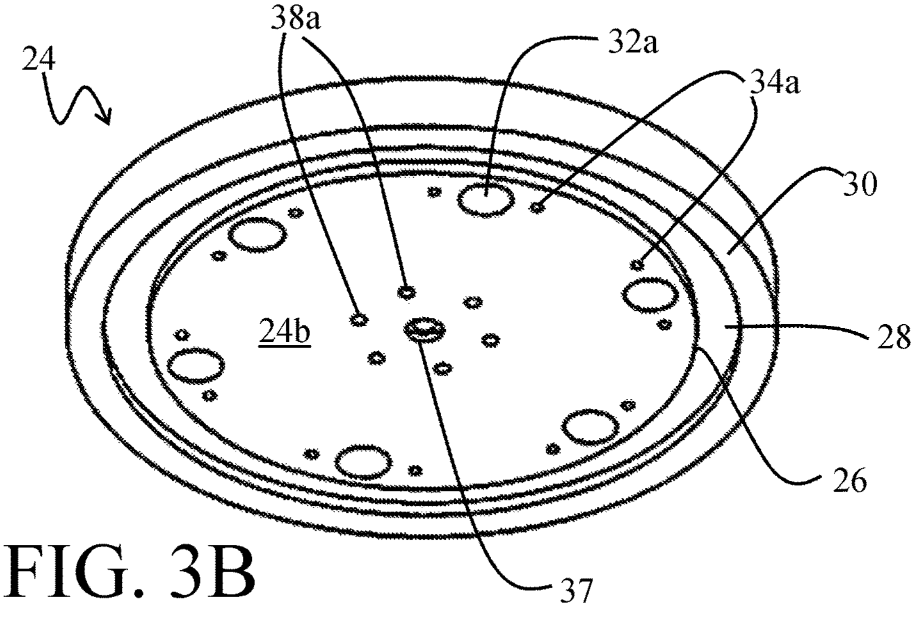
FIG. 3B is a depiction of the bottom surface of the lid.

The lid 24 can be seen in FIGS. 3A-B. FIG. 3A depicts the top surface 24*a* of the lid 24, while FIG. 3B depicts the bottom surface 24*b*. As shown in FIG. 3B, the bottom surface 24*b* of the lid 24 features a central disc 26, circumscribed by a groove 28. The groove 28 is, in turn, surrounded by a lip 30 radially disposed from the groove. The groove 28 engages the proximal end 22*p* of the Dewar container 22 such that the proximal end 22*p* is inserted between the central disc 26 and the lip 30 so as to nest within the groove 28.

As can be seen in both FIGS. 3A and 3B, regions of the lid form transverse apertures or openings such that the plurality of openings 32*a* extends entirely through the thickness of the lid 24. Optionally, the openings 32*a* are roughly equidistantly spaced around the periphery of the central disc 26. A pair of diametrically opposed, smaller recesses 34*a* flank each of the openings 32*a*, such that a straight line defined by the center of the two smaller apertures includes the center point of the opening 32*a*. The holes 34*a* are provided to anchor the lid brackets. In an embodiment, four holes are utilized: one for the pump outlet; one for the liquid return line; one for the level sensor; and one for the filling line. Two additional holes are provided for flexibility in assembly and seeing into the Dewar container.

At the center of the lid 24 is a region forming a center transverse aperture 36*a*. The center transverse aperture 36*a* is adapted to slidably receive the shaft 20, so as to allow the shaft to pass through the lid into the interior of the Dewar container 22. On the second or bottom surface 24*b* of the lid 24, the aperture 36*a* is surrounded by a countersunk annular groove or recessed ring 37 that has a slightly wider diameter than the aperture 36*a*. The recessed ring 37 aids in assembly of the device 10, and its purpose is discussed infra. Encircling, but spatially and radially disposed from the aperture 36*a* is a plurality of through holes 38*a*, such that the holes extend transversely through the lid. The through holes 38*a* aid in assembly of the first end of the device, which is described in detail below. The through holes 38*a* are preferably spaced equidistantly in a circle around the aperture 36*a*. In the embodiment depicted in FIGS. 3A-B, there are six through holes.

Figure 4:
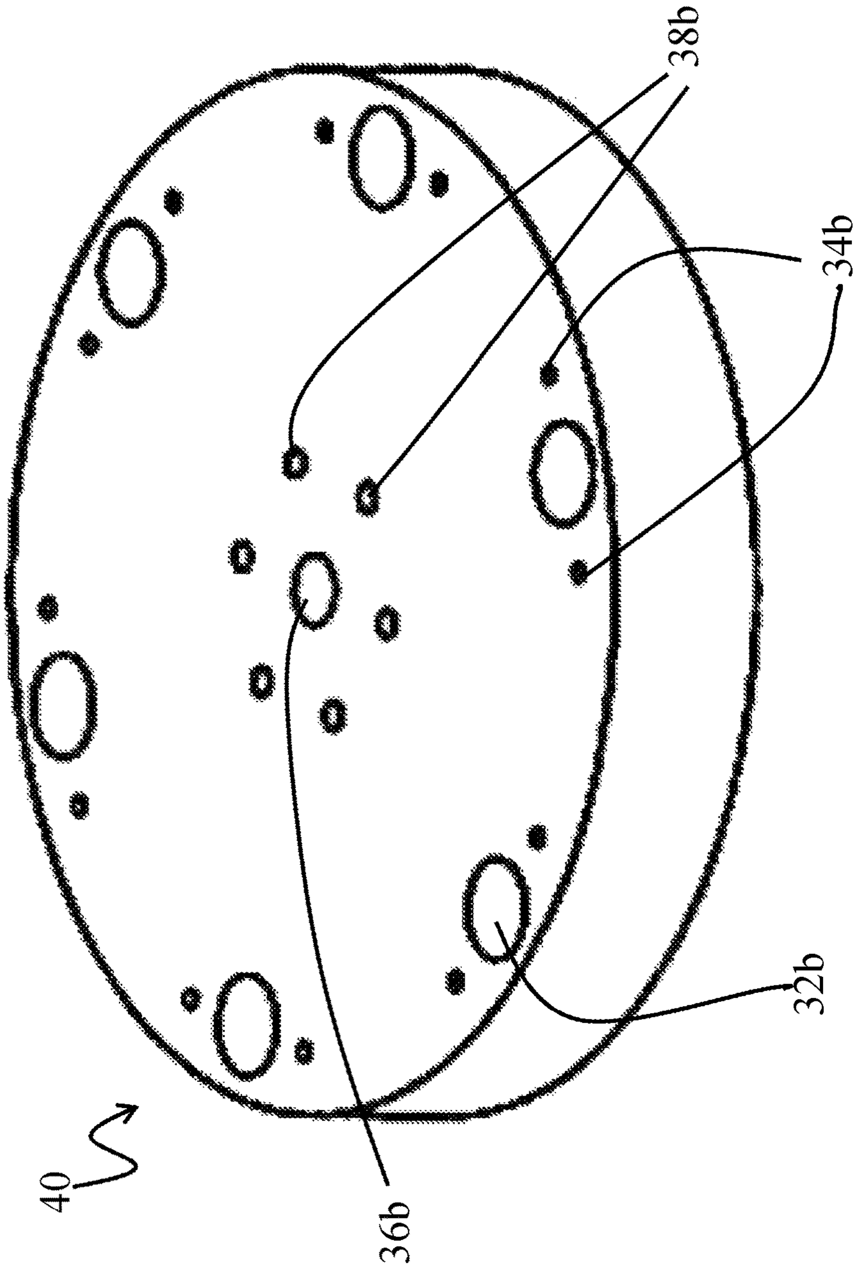
FIG. 4 is a perspective view of the insulator disc.

Below the lid 24 is an insulator disc 40, shown in FIG. 4. The insulator disc 40 has a diameter roughly equal to the inside diameter of the Dewar container 22, or approximately the same diameter as the central disc 26 so as to frictionally engage the inside of the Dewar container. The insulator disc 40 contains many of the same structures as the lid 24 including a plurality of openings 32*b*, recesses 34*b*, aperture 36*b*, and through holes 38*b*, such that when the insulator disc 40 and lid are positioned on the Dewar container, the structures of each of these objects lie in registration with each other. The size and position of each of these features is substantially the same as that of the corresponding features on the lid 24. However, the central aperture 36*b* of the disc has a diameter that is approximately the same size as that of the recessed ring 37 formed into the bottom surface 24*b* of the lid 24. This attribute facilitates assembly of the first end 12 components, which will be discussed below.

The insulator disc 40 is made of a thermally insulating material. PVC hard foam is a suitable material for the insulator disc 40 because of its superior insulation properties and because it is relatively inexpensive. In an embodiment of the invention, the insulator is removably attached to the lid.

The insulator disc 40 serves a multitude of purposes. Primarily, the insulator disc 40 prevents heat transfer between the lid 24 and the interior of the Dewar container 22. (Heat can crack the lid, lead to a build-up of ice, and accelerate the loss of cryogenic liquid.) Additionally, the insulator disc 40 prevents the extremely cold temperatures of the cryogenic liquid in the Dewar container 22 from affecting the motor 16. Furthermore, the insulator disc 40 frictionally engages the interior of the Dewar container 22, ensuring that the lid 24 snugly and evenly covers the open end of the Dewar container 22.

Figure 5A:
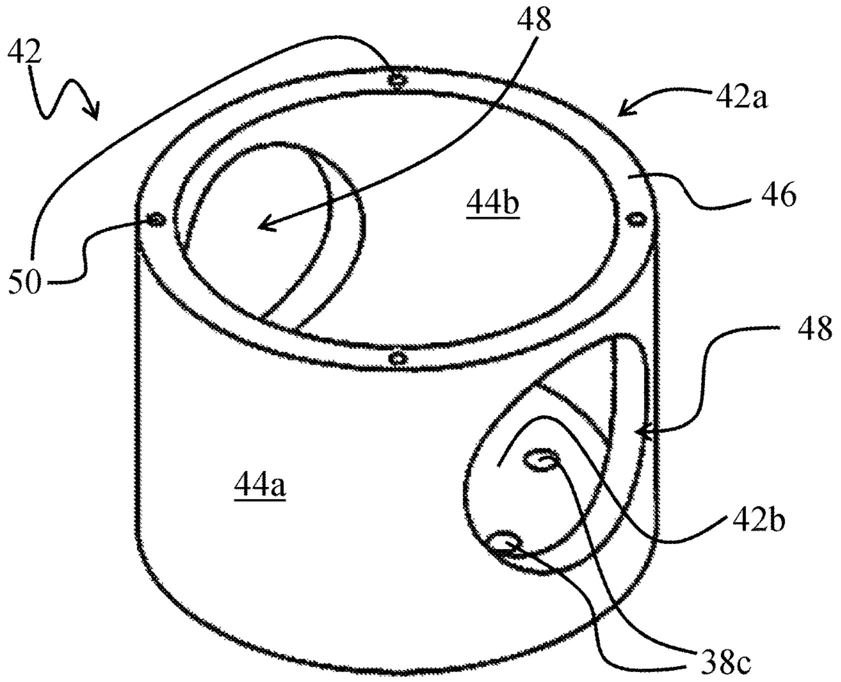
FIG. 5A is a perspective view of the alignment canister.

An alignment canister 42 rests upon, so as to be supported by, the lid 24. The alignment canister 42, as depicted in FIG. 5A, is a cylinder with an open top 42*a*. The canister 42 also features a floor 42*b* with a plurality of through holes 38*c* and a central aperture 36*c* (shown in FIG. 5B). The size and number of the through holes 38*c* is the same as the size and number of the through holes 38*a* in the lid 24 and the through holes 38*b* in the insulator disc 40 so as to lie in registration with the holes in the lid and disc. Further, the central aperture 36*c* is the same size as the aperture 36*a* on the top surface 24*a* of the lid 24.

Figure 2A:
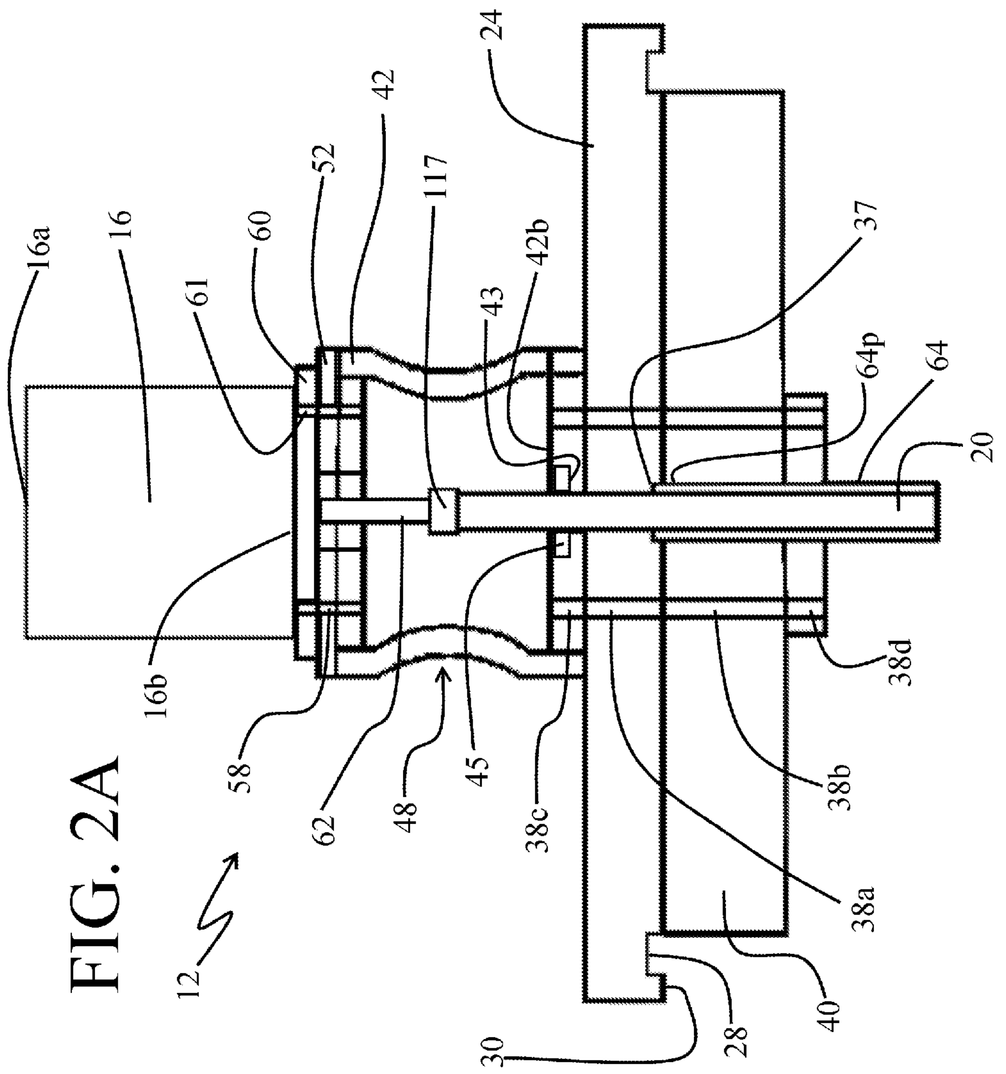
FIG. 2A is a detail view of the first end of the cryogenic pump as depicted in FIG. 1B.
Figure 5B:
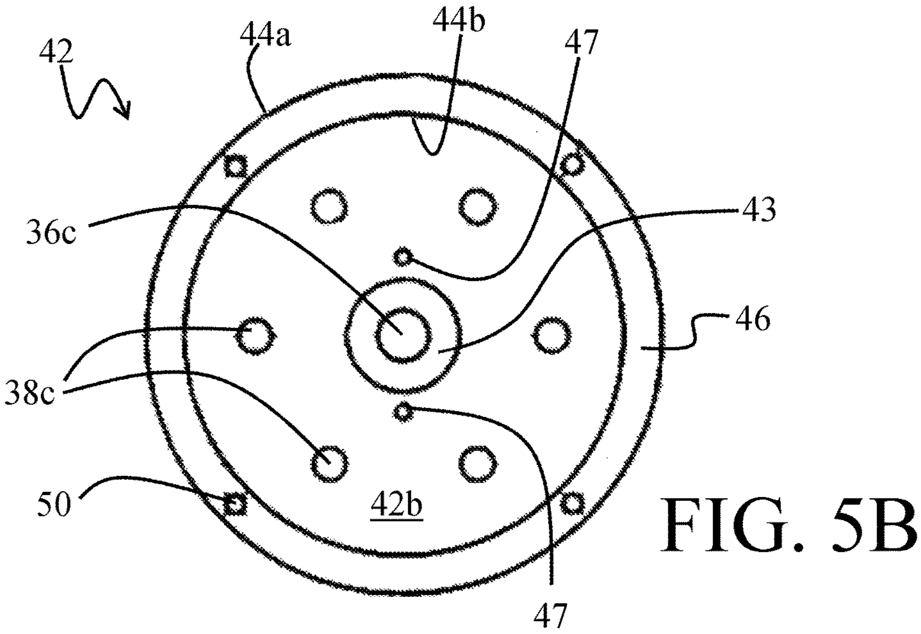
FIG. 5B is a plan view of the alignment canister.

As shown in FIG. 5B, circumscribing the central aperture 36*c* is a groove 43, adapted to receive a first bearing 45 (shown in FIG. 2A). The first bearing 45 can optionally be secured with a bearing bracket. Docks 47 for securing the bearing bracket (not shown) are provided on the floor 42*b* of the alignment canister 42. The bearing bracket is similar in shape as the lid bracket discussed below. Essentially, the bearing bracket is a flat substrate with threaded holes on each side through which a screw can be inserted into the docks 47. The center of the bearing bracket is notched to accommodate the shaft 20.

Extending upwardly from the periphery of the floor 42*b* is an axially extending perimeter wall 44 with an interior surface 44*a* and an exterior surface 44*b*. The distance between the interior surface 44*a* and the exterior surface 44*b* defines the thickness of the wall 44. At the top 42*a* of the canister 42, the thickness of the wall 44 defines a flat shelf surface 46. The perimeter wall 44 contains a plurality of windows 48 that extend through the thickness of the wall. These windows 48 provide access to the interior of the canister 42 during assembly of the device 10. The windows 48 also permit monitoring of the top bearing and motor shaft and allow water to easily evaporate from the inside of the alignment canister 42. As depicted in FIG. 5A, there are two circular windows 48 diametrically opposed to each other, each having a diameter of approximately two inches. More or less windows 48 could be provided, but the inventors suggest at least two, each with a diameter of at least two inches, to provide adequate access to the interior of the alignment canister 42 and adequate ventilation for evaporation. Formed into the flat shelf surface 46 is a plurality of coupling points 50. FIGS. 5A-B depict female couplings that extend into the thickness of the perimeter wall 44 towards the floor 42*b*.

Figure 6A:
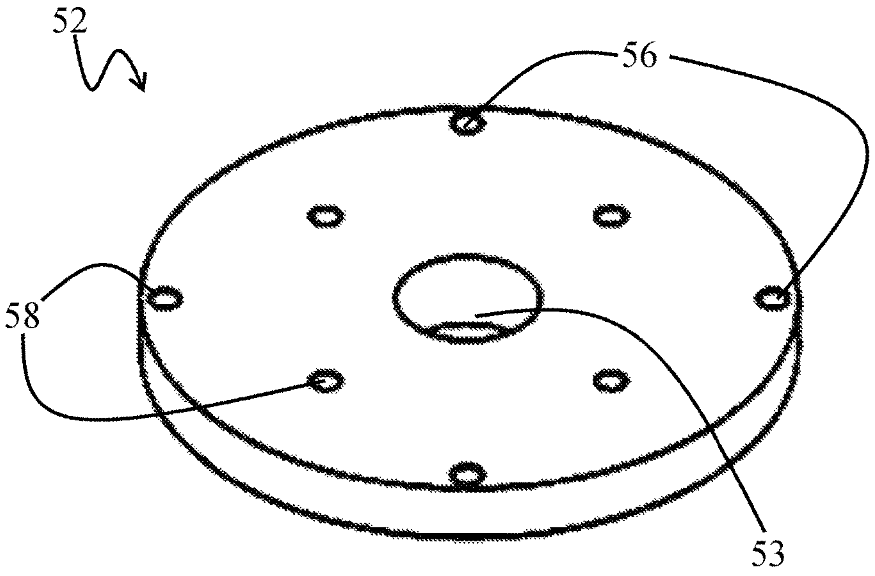
FIG. 6A is a perspective, top view of the alignment plate.
Figure 6B:
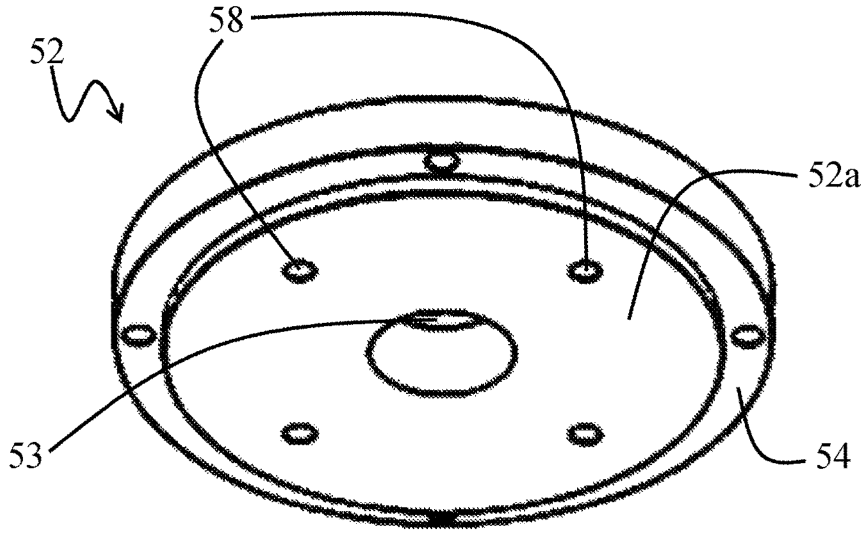
FIG. 6B is a perspective, bottom view of the alignment plate.

As depicted in FIG. 2A, an alignment plate 52 is supported by the top of the alignment canister 42. Perspective views of the alignment plate 52 are depicted in FIGS. 6A-B. As depicted in FIG. 6B, the alignment plate 52 has an upwardly facing surface (shown in FIG. 6A) and a downwardly facing surface (shown in FIG. 6B). The downwardly facing surface defines an axially extending surface 52*a*, with its periphery medially disposed from the periphery of the plate 52. The diameter of this axially extending surface is less than the inside diameter of the canister 42 so as to be received by the opening of the canister. The region of the plate between the periphery of the axially extending surface 52*a* and the periphery of the plate defines a surface or periphery region 54 countersunk from the surface 52*a* and which circumscribes the axially extending surface 52*a*. This periphery region engages the flat shelf surface 46. The periphery region 54 contains a plurality of holes 56. The number and position of the holes 56 are designed to match the number and position of the coupling points 50 on the canister 42. In this way, an attachment means, such as a screw or pin, can be inserted through the holes 56 and into the coupling points 50 to attach the alignment plate 52 to the alignment canister 42.

The alignment plate 52 features a central passage 53 that accommodates insertion of the motor's driveshaft. Circumscribing the central passage 53 in the alignment plate 52 is a plurality of mounting points 58, which allow for the motor 16 to be mounted to the alignment plate 52. As depicted in FIGS. 6A-B, there are four mounting points 58.

The motor 16 can be any suitable motor for pumping applications. Preferably, the motor 16 is DC-driven so that the pump speed can easily be controlled by an adjustable DC power supply; however, AC-driven motors can also be used with the present invention. The inventors have found that a 26 frame PMDC motor (24V), available from Bison Gear & Engineering Corp. (St. Charles, Ill.), to be a suitable motor for the present invention. Supplying the motor with a voltage of 20V, flow rates as high as about 11 L/min were achieved with a pump head of approximately 0.4 m. At about 10V, flow rates as low as about 0.1 L/min were attainable with a pump head of about 1.2 m. At about 15V, the pump could operate at flow rate of about 1.5 L/min while maintaining a pump head of about 2 m. As with typical centrifugal pumps, pump head decreased with increasing flow rates at all voltages.

As shown in FIG. 2A, the motor 16 features a mounting plate 60 which is positioned between the motor and the alignment plate 52. The plate 60 defines complementary mounting points 61 that engage the mounting points 58 on the alignment plate 52. In some cases, the mounting points 58, 61 are threaded channels that are secured together using a nut and bolt. Alternatively, the mounting plate 60 and alignment plate 52 can be joined using pins, a pin and groove combination, or hooks and clasps. Additionally, the motor 16 and alignment plate 52 can be permanently attached to each other, such as through welding, adhesive, or another fusion process.

The motor 16 has a first end 16*a* and a second end 16*b*. At the first end 16*a*, the motor is electrically connected to a power source. The second end 16*b* features a drive shaft 62 that is mechanically coupled to the shaft 20.

Shaft Detail

As can be seen in FIG. 2, the proximal end 20*p* of the shaft 20 extends from the driveshaft 62 through the coaxially aligned apertures 36*a*, 36*b*, 36*c* in the alignment canister 42, lid 24, and insulator disc 40. As can be seen in FIG. 1B, the distal end 20*d* of the shaft terminates at the pump 18. In this instance, the pump is coaxially arranged with the longitudinal axis of the Dewar container.

FIG. 7A shows the distal end 20*d* of the shaft 20 having a portion 63 with a narrower diameter than the remainder of the shaft 20. As shown in FIG. 7B, formed on the narrow portion 63 of the shaft 20 is a keyway 65. The keyway 65 is a semi-cylindrical, recessed channel designed to engage the components of the pump 18 described below through the use of a cylindrical key (not shown). Specifically, the keyway is a cylindrical channel formed in the shaft end, impeller, and inducer. Half of this channel is in the shaft, half in the impeller and inducer. When assembled, a single cylindrical pin holds the three pieces in position as a means for ensuring that all of these structures co-rotate.

Figure 8:
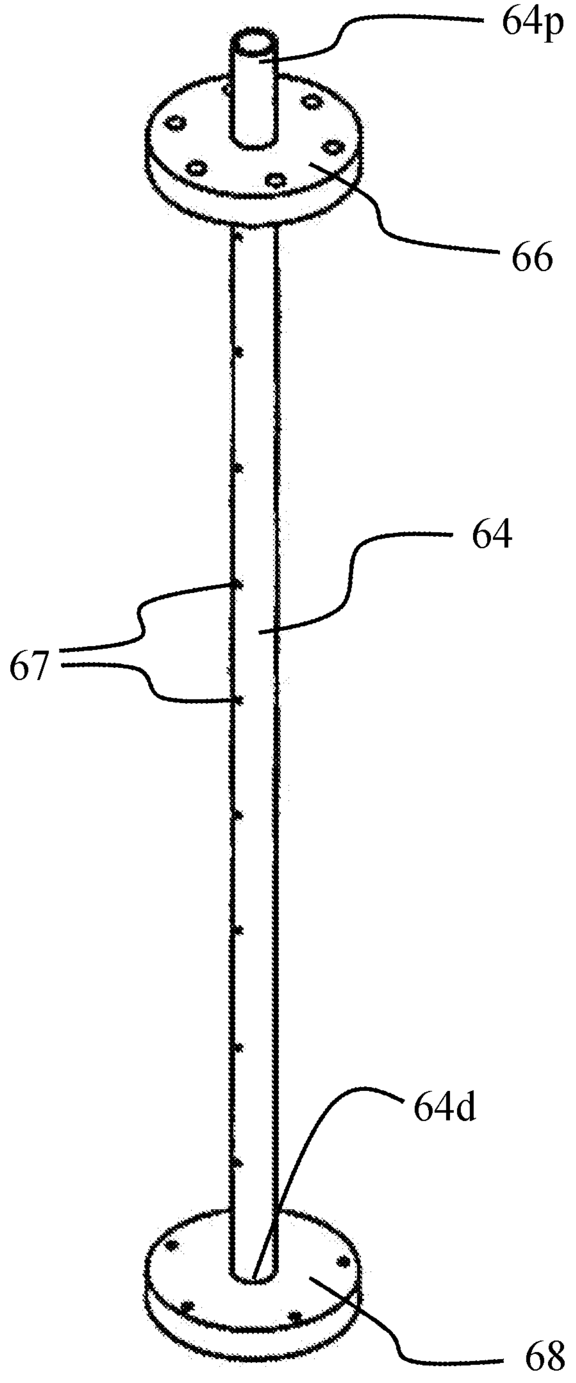
FIG. 8 depicts the support tube with upper and lower flanges.

Surrounding the shaft 20 is a conduit serving as a support tube 64. The support tube 64 slidably receives the shaft 20. As can be seen in FIG. 8, the support tube 64 has a proximal end 64*p* and a distal end 64*d*. As shown in FIG. 8, between the proximal end 64*p* and the distal end 64*d* are regions of the shaft defining a plurality of vents 67 that are spaced at regular intervals along longitudinally extending regions of the tube. The vents 67 allow for gas or cryogenic liquid to escape from the support tube 64 so as to prevent as much cryogenic liquid from reaching the lid 24 as possible. As such, the vents provide a means for minimizing the level of cryogenic fluid along vertical aspects of the shaft. One such means includes the use of gravity to cause fluid exiting the vents to sink toward the bottom of the Dewar container. The vents 67 can optionally be closed with screws, pins, or plugs.

As can be seen in FIG. 2A, the proximal end 64_p_ of the support tube 64 is inserted through the central aperture 36_b_ of the insulator disc 40. As stated above, the central aperture 36_b_ of the insulator disc 40 is slightly larger than the central apertures 36_a_, 36_c_ of the lid 24 and alignment canister 42 to accommodate the support tube 64. The proximal end 64_p_ of the support tube 64 engages the recessed ring 37 on the bottom surface 24_b_ of the lid 24. Thus, the support tube 64 nests within the underside surface of the lid 24. This confers support to the tube so as to prevent it from yawing, or otherwise moving during shaft rotation.

Spatially disposed of the proximal end 64_p_ of the tube 64 is an upper flange 66. The upper flange 66 anchors the pump 18 to the first end 12 of the device 10. The upper flange 66 also maintains the coaxial arrangement of the axis of the alignment canister 42 with the support tube 64, while a lower flange 68 maintains the coaxial arrangement of the alignment canister 42 with the components of the pump 16 below. Thus, alignment among the motor 16, shaft 20, and pump 18 is ensured.

Figure 9:
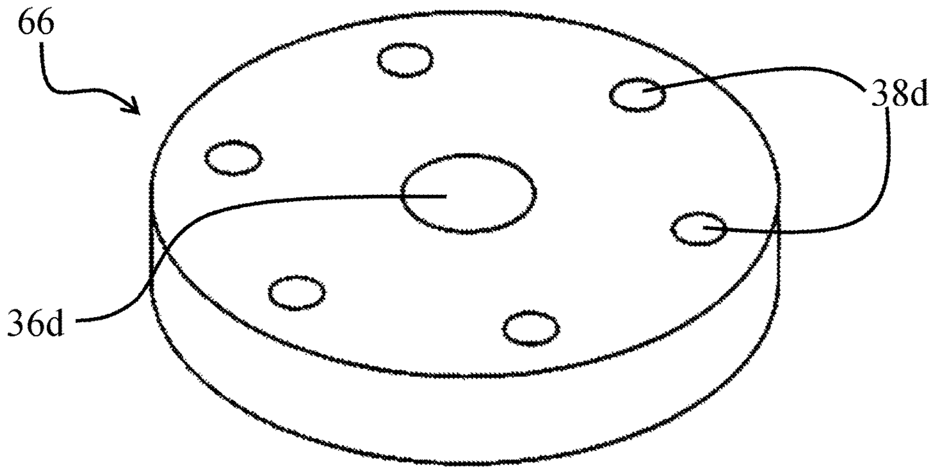
FIG. 9 depicts the upper flange.

The upper flange 66 (depicted in FIG. 9) has the same cross section geometry as the lid 24, insulator disc 40 and alignment canister 42 so as to facilitate its assembly with those other elements. In the illustrated embodiment, the upper flange 66 is generally circular in shape and contains a central aperture 36_d_. The diameter of the central aperture 36_d_ is large enough to accommodate the support tube 64, which makes the diameter approximately the same size as the central aperture 36_b_ in the insulator disc 40 and as the ring 37 in the bottom surface 24_b_ of the lid 24. The upper flange 66 also contains regions defining a plurality of through holes 38_d_ with the through holes 38_d_ being the same in size and number as the through holes 38_a_, 38_b_, 38_c_ in the lid 24, insulator disc 40, and alignment canister 42. The through holes 38_d_ facilitate assembly of the first end 12 of the device 10.

Figure 10:
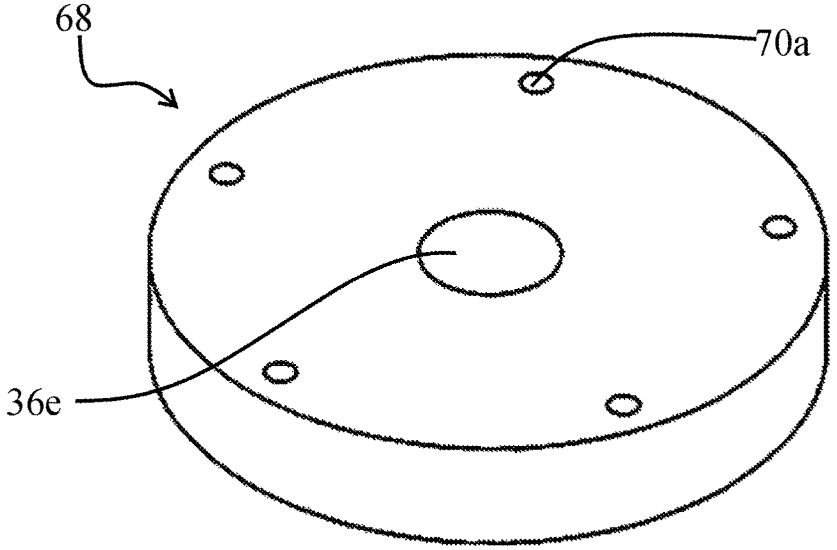
FIG. 10 depicts the lower flange.

The lower flange 68 (depicted in FIG. 10) is located at the distal end 64_d_ of the support tube 64. The lower flange 68 is substantially similar to the upper flange 66 in that it is generally circular in shape and contains a central aperture 36_e_. The central aperture 36_e_ is large enough to accommodate the support tube 64. The lower flange 68 has a plurality of through channels 70_a_. Like the through holes 38_a-d_ that secure the components of the first end 12 together, the through channels secure the components of the second end 14 together. As depicted in FIG. 10, the lower flange 68 has five through channels 70_a_.

The upper flange 66 and the lower flange 68 are welded, or otherwise joined, to the support tube 64. The upper flange 66 is welded in a position spatially disposed of the proximal end 64_p_ of the support tube 64 so that the support tube can be inserted through the insulator disc 40 and partially into the lid 24. The lower flange 68 is welded such that the distal end 64_d_ of the support tube 64 is flush with the bottom surface of the lower flange 68.

Pump Detail

The pump 18 is comprised generally of a pump housing 72, an impeller 74, an inducer 76, a gas release plate 78, and a lower bearing plate 80.

Figure 11A:
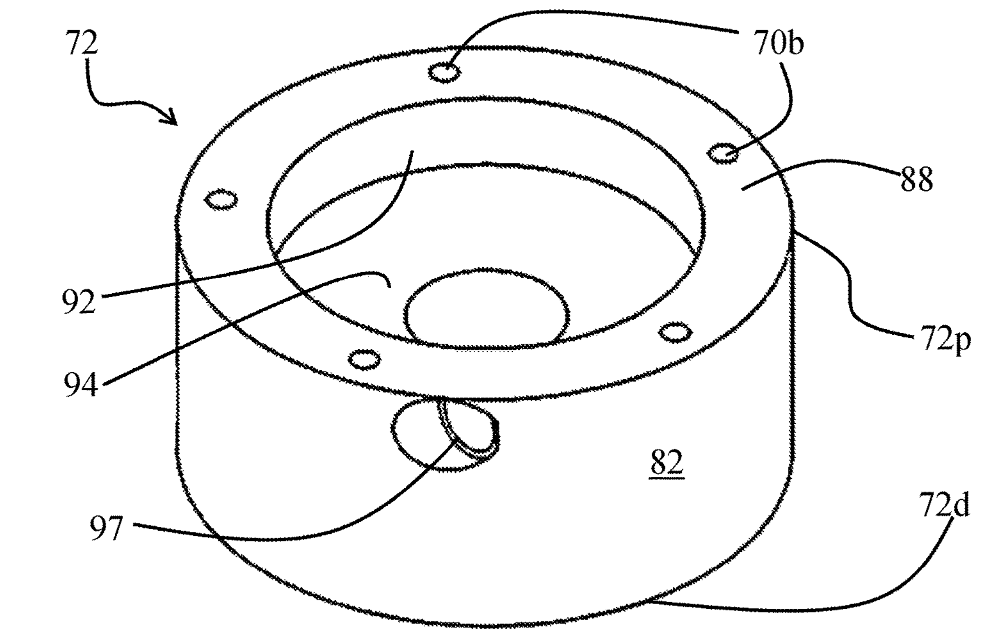
FIGS. 11A-C depict various views of the pump housing.
Figure 11B:
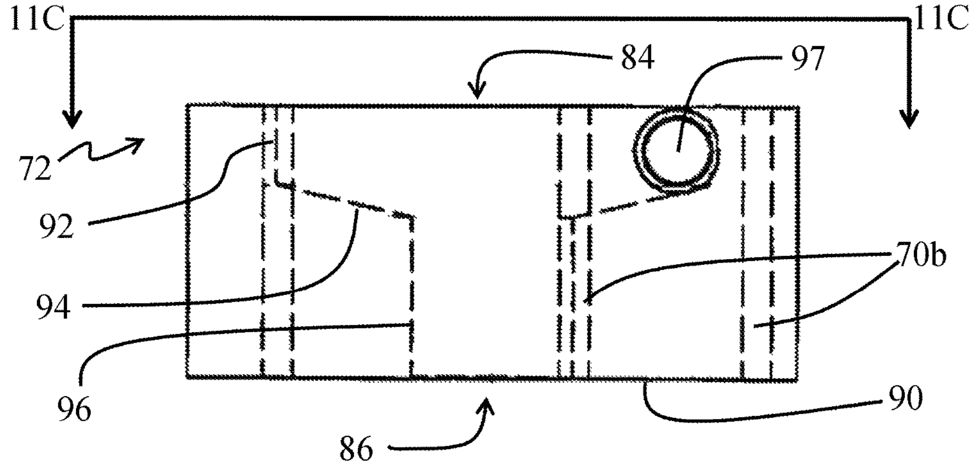
Figure 11C:
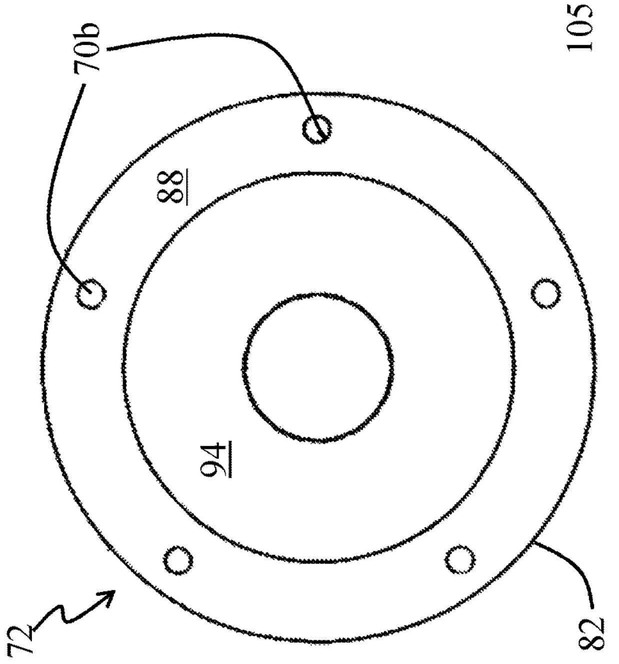

The pump housing 72, as depicted in FIGS. 11A-C, defines a passage through the housing and has an open proximal end 72_p_ and an open distal end 72_d_. As can be seen in FIG. 11A, the pump housing 72 features an exterior surface 82 between the proximal end 72_p_ and the distal end 72_d_ that is substantially cylindrical. As can be seen in the cutaway view FIG. 11B of the housing, the proximal end 72_p_ and the distal end 72_d_ both contain circular openings with a first opening 84 at the proximal end 72_p_ and a second opening 86 at the distal end 72_d_. The first opening 84 is wider in diameter at its rim than the second opening 86. The sides of the first opening converge in a frusto-conical configuration to approximately the midpoint of the housing body. At this approximate midpoint, the passage walls stop converging and rather extend directly (in an axial direction) to the distal end of the housing.

Surrounding the first opening 84 is a proximal surface 88 as shown in FIG. 11A. Surrounding the second opening 86 is a distal surface 90 (FIG. 11B). Regions of the proximal surface define longitudinally extending apertures or through channels 70_b_ which extend through the pump housing 72 from the proximal surface 88 to the distal surface 90. The size and number of through channels 70_b_ are the same as the size and number of through channels 70_a_ in the lower flange 68.

As discussed supra, the interior region of the pump housing 72 features a first cylindrical section 92 in fluid communication with a frustoconical section 94, which is in fluid communication with a second cylindrical section 96. The first cylindrical section 92 has the same diameter as the first opening 84. The second cylindrical section 96 has the same diameter as the second opening 86. The frustoconical section 94 tapers in diameter from the first cylindrical section 92 to the second cylindrical section 96. Further, as shown in FIG. 11B, the first cylindrical section 92 is shorter than the second cylindrical section 96 because of the relative size of the pump components that each section contains. A liquid port 97 is formed into the first cylindrical section 92. The liquid port 97 extends through to the exterior surface 82 of the pump housing 72. FIGS. 11A-B depict a circular liquid port 97 that has a diameter roughly equal to the height of the first cylindrical section 92. This port is positioned within the structure of the housing at an angle to the cross section of the housing to maximize fluid flow from an impeller spinning within the first cylindrical section 92. The port 97 is roughly tangential to the curvature of the first cylindrical section 92 so as to provide a port 97 that is parallel to the direction of liquid flow.

Figure 2B:
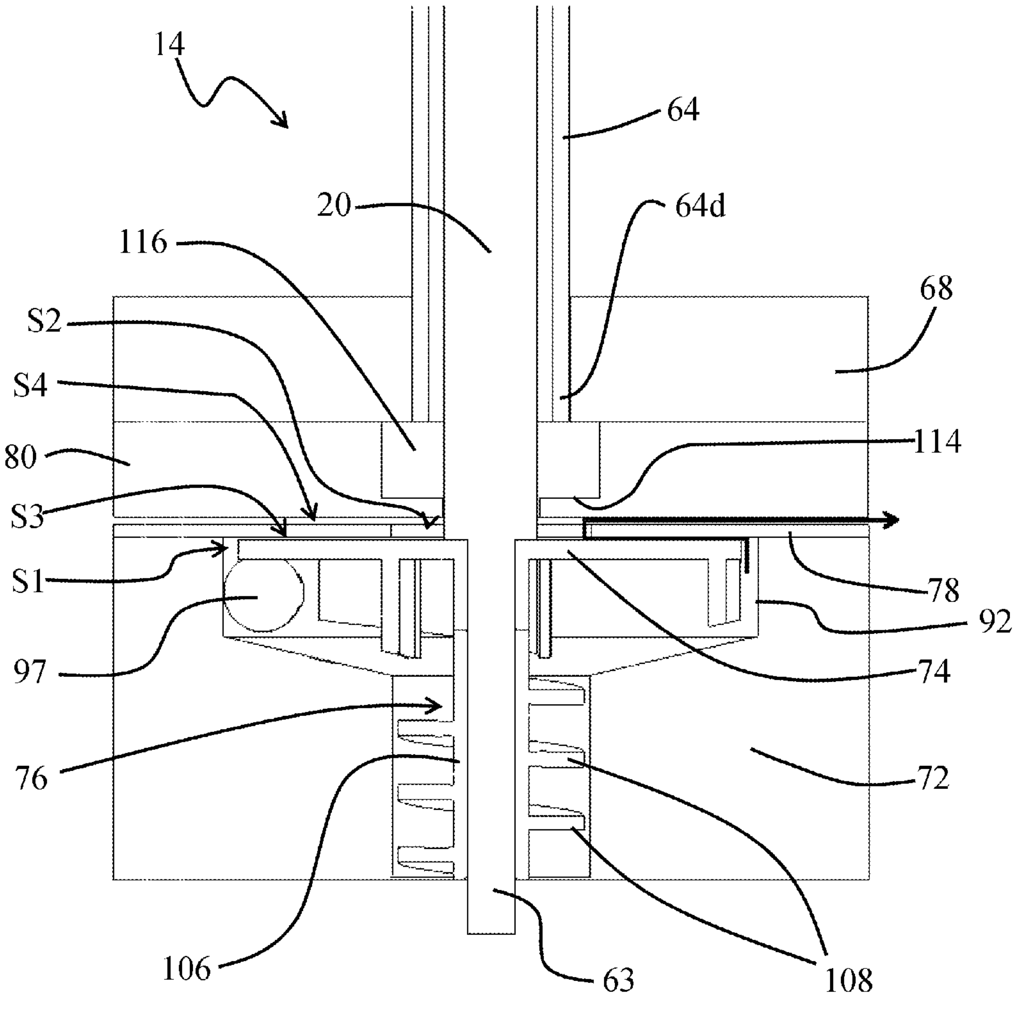
FIG. 2B is a detail view of the second end of the cryogenic pump as depicted in FIG. 1B.
Figure 12:
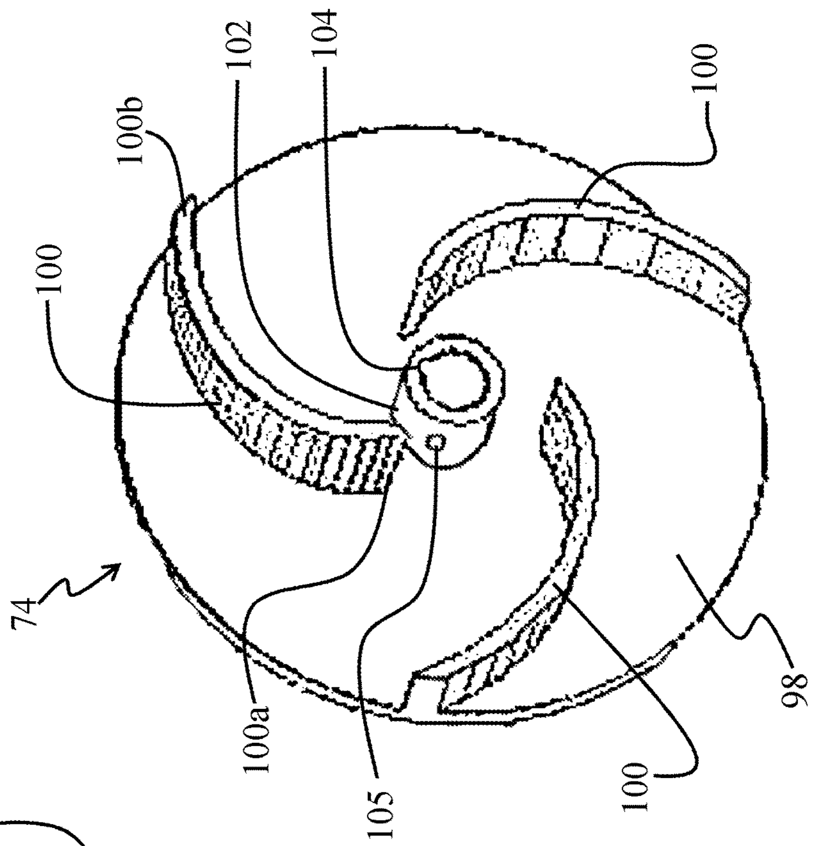
FIG. 12 depicts the pump impeller.

The first cylindrical section 96 is adapted to receive the impeller 74, such that the section 96 substantially encircles the impeller. The structure of the impeller 74 can be seen in FIG. 12. The impeller 74 is comprised of a disc 98 upon which a plurality of vanes 100 is mounted. As depicted in FIG. 12, the disc 98 is a thin, flat, and circular substrate featuring three vanes 100. Turning to FIG. 2B, the diameter of the disc 98 is the smaller than the diameter of the first cylindrical section 92 such that a first space "S1" is circumferentially provided around the disc 98. Returning to FIG. 12, each vane 100 on the disc 98 has a first end 100_a_ and a second end 100_b_. The first end 100_a_ of each vane begins at the same radial distance away from the center of the disc 98. Each vane 100 extends from its first end 100_a_ in arcuate fashion until it terminates in the second end 100_b_ at the perimeter of the disc. The curvature of the vanes is approximately an Archimedes spiral. The vanes further protrude axially from the surface of the disc with the first end 100_a_ extending a further axial distance than the second end 100_b_.

At the center of the disc 98, a collar 102 extends axially from the surface of the disc 98. The collar 102 accommodates the narrower portion 63 of the shaft 20. A keyway 104 is formed into the interior of the collar 102. The keyway 104 is a semi-cylindrical, recessed channel that accommodates that complements the keyway 65 on the narrow portion 63 of the shaft 20. A cylindrical key is inserted between the complementary keyways 65, 104 so as to provide a means for transferring mechanical energy created in the motor 16, through the shaft 20, and finally to drive the impeller 74. A longitudinally extending region of the collar forms a threaded aperture 105 adapted to receive a screw for frictional engagement with an opposing surface of the shaft. This screw, upon so engaged, reversibly fastening the impeller to the shaft so as to prevent the impeller from traveling along the shaft in the pump housing. The keyways, key, and screw provide a means to hold the shaft, impeller and inducer together and in registration.

As stated supra, cavitation is the most prominent reason for cryogenic pump failure. The present invention substantially reduces the problem of cavitation in two ways. First, an inducer 76, placed below the impeller 74 and within the second cylindrical section 96 of the housing 72, increases the pressure on the cryogenic liquid at the impeller 74, preventing the formation of gas bubbles. Second, the gas release plate 78 is placed above the impeller 74 to allow any gases generated at the impeller to flow away from the pump without obstructing flow of the cryogenic liquid out of the pump 18.

Figure 13:
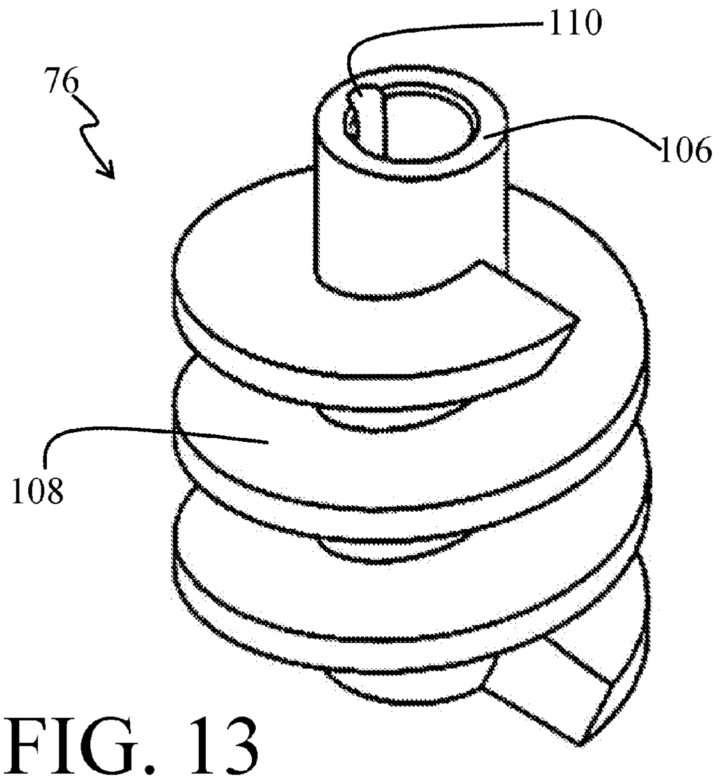
FIG. 13 depicts the inducer.

The inducer 76 is a screw conveyer that forces the cryogenic liquid into the impeller region of the pump. As depicted in FIG. 13, the inducer 76 has a central sleeve portion 106. A thread 108 spirals around the sleeve portion 106. The thread 108 on the inducer 76 shown in FIG. 13 makes three complete turns around the sleeve portion 106; however, more or less turns can be used without departing from the spirit of the present invention. The diameter of the inducer 76 (i.e., diameter of the sleeve 106 plus the width of the thread 108) is the same or slightly smaller than the diameter of the second cylindrical section 96 of the pump housing 72. Like the collar 102 of the impeller 74, a keyway 110 is formed into the interior of the sleeve portion 106, along with a threaded aperture adapted to receive a locking bolt or screw. The keyway 110 engages the key 65 on the narrow portion 63 of the shaft 20 and allows mechanical energy to be transferred from the shaft 20 to the inducer 76. The inducer 76 increases the pressure on the cryogenic liquid entering the impeller 74, thereby increasing the local boiling point of the liquid. Thus, the inducer 76 helps to avoid cavitation by preventing the formation of gas in the impeller 74.

Figure 14:
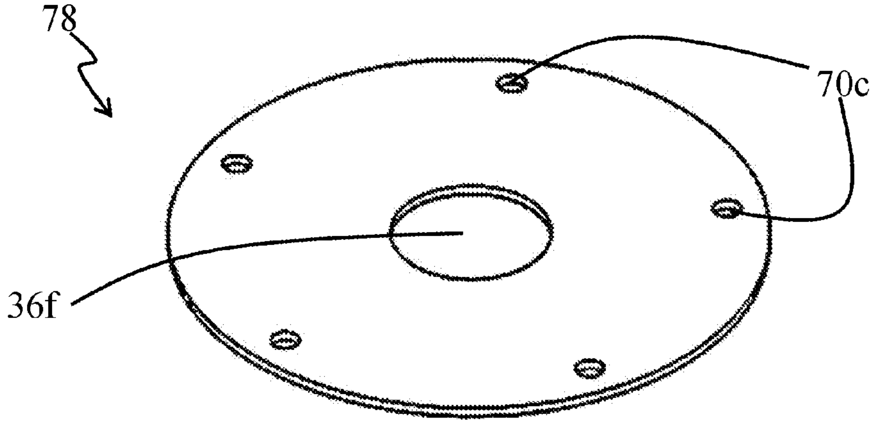
FIG. 14 depicts the gas release plate.

The second feature responsible for the reduction in cavitation is the gas release plate 78. As depicted in FIG. 14, the gas release plate 78 is a thin, round disc located above the impeller 74. The diameter of the gas release plate 78 is the same as the outer diameter of the pump housing 72. The gas release plate 78 also features a plurality of transversely extending apertures or through channels 70*c* formed along the periphery of the gas release plate. The size and number of the through channels 70*c* is the same as the size and number of through channels 70*a*, 70*b* in the lower flange 68 and the pump housing 72. An aperture 36*f* traverses the thickness at the center of the gas release plate 78. The aperture 36*f* has approximately twice the diameter of the shaft 20, thereby providing a second space S2 between the shaft 20 and the circumference of the aperture (depicted in FIG. 2B).

Over time some gas bubbles will inevitably form in the impeller region of the pump. In order to preserve the functioning of the pump, those gas bubbles must be allowed to escape from the impeller 74. Thus, the gas release plate 78 provides a means of egress the gas bubbles from the interior of the pump without obstructing the liquid port 97.

Operation of the gas release plate 78 is facilitated by additional spaces provided above and below the gas release plate 78 as shown in FIG. 2B. A third space "S3" is provided between the central disc 98 and the gas release plate 78. The third space S3 is set during assembly of the device as described below. A fourth space "S4" is then provided between the gas release plate 78 and the lower bearing plate 80. The fourth space S4 is provided using washers (not shown) during assembly of the device.

FIG. 2B shows how the gas release plate allows removal of gas bubbles from the impeller region. As the impeller 74 spins, the impeller vanes 100 impart a radially directed force on the gas bubbles, causing the bubbles to move away from the center of the impeller 74 and toward the walls of the first cylindrical region 92. At this juncture, the bubbles are actuated via mechanical means, and not by pressure gradient.

Once the gas bubbles reach the wall of the first cylindrical section 92, their relative density allows them to float upwardly through the first space S1 between the central disc 98 of the impeller and the wall of the first cylindrical section 92. The gas bubbles then move transversely through the third space S3 until they reach the shaft 20. The transverse flow of the bubbles results from the pressure gradient formed above the impeller as a result of the frictional forces between the impeller and the liquid. The centrifugal forces cause the pressure gradient to point radially away from the shaft. Because the bubbles are less dense than the liquid, they flow opposite the direction of the pressure gradient. The bubbles again move upwardly through the second space S2 and then transversely across the fourth space S4, thereby exiting the pump housing 72.

Figure 15:
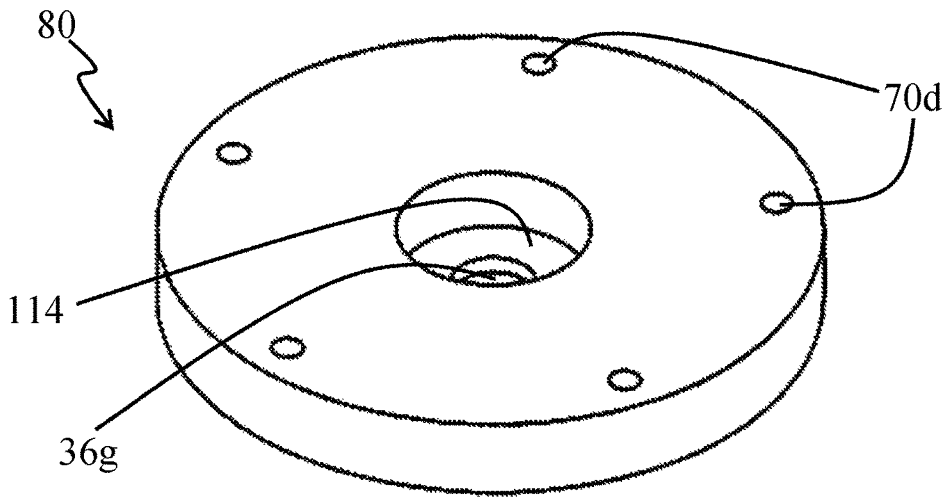
FIG. 15 depicts the lower bearing plate.

The final component of the pump 18 is the lower bearing plate 80. As shown in FIG. 15, the lower bearing plate 80 is a circular disc having the same diameter as the pump housing 72 and the gas release plate 78. A plurality of through channels 70*d* are formed around the periphery of the lower bearing plate 80. At the center of the lower bearing plate is an aperture 36*g* that accommodates the shaft 20. A second recessed groove 114 encompasses the aperture 36*g*. A second bearing 116 is placed in the second groove 114. The second bearing 116 in the lower bearing plate 80 works in conjunction with the first bearing 45 in the alignment canister 42 to assure that the shaft 20 spins in a stable fashion.

Assembly and Operation

To assemble the first end 12 of the device 10, the insulator disc 40, lid 24, and alignment canister 42 are arranged such that the through holes 38*a-c* and central apertures 36*a-c* align or are otherwise in registration. These components are then temporarily joined using a fastener, such as a bolt and a nut. Alignment of the through holes 38*a*, 38*b* and apertures 36*a*, 36*b* in the lid 24 and the insulator disc 40 will bring the openings 32*a*, 32*b* and recesses 34*a*, 34*b* into alignment as well, which is important for operation of the device. The first bearing 45 is placed in the groove 43 formed into the floor 42*b* of the alignment canister 42.

The drive shaft 62 of the motor 16 is inserted through the central passage 53 of the alignment plate 52. The mounting points 61 in the mounting plate 60 are aligned with the mounting points 58, and the motor 16 and the alignment plate 52 are secured together. The alignment plate 52 is then attached to the alignment canister 42, using fasteners, such as screws, bolts, or pins, inserted through the holes 56 in the alignment plate into the coupling points 50 formed into the flat shelf surface 46 of the alignment canister 42.

The shaft 20 is inserted into the welded support tube 64, upper flange 66, and lower flange 68 combination. The shaft 20 and support tube 64 are then inserted into the central apertures 36*a-c* of the insulator disc 40, lid 24, and alignment canister 42 until the upper flange 66 abuts the insulator disc 40 and the proximal end 64*p* of the support tube 64 abuts the recessed ring 37. The fasteners are inserted through the through holes 38*d* in the upper flange 66, and the lid 24, insulator disc 40, alignment canister 42, and upper flange 66 are firmly secured together. The shaft 20, being freely movable within the support tube 64, is brought into close proximal relation to the driveshaft 62 of the motor 16.

The shaft 20 and drive shaft 62 are loosely coupled together using a flexible coupling 117, such as the double beam clamp, manufactured by Lovejoy, Inc. (Downers Grove, Ill.). The double beam clamp has two screw clamps at either end of the coupling. The first clamp attaches to the drive shaft 62, while the second clamp attaches to the shaft 20. The tightness of the clamps can be adjusted using Allen wrenches on the screws. When the driveshaft 62 and shaft 20 are first joined at the coupling 117, they are loosely held together so that the shaft positioning can be adjusted during assembly of the second end 14 of the device 10. The windows 48 in the alignment canister 42 allow for the assembler to manipulate the shaft 20, driveshaft 62, and coupling 117.

To assemble the second end 14 of the device 10, bolts, screws, or other fastening means are inserted in the through channels 70*a* in the lower flange 68. Then, the second bearing 116 is inserted into the second groove 114 in the lower bearing plate 80. The central aperture 36*g* and the through channels 70*d* are aligned with the shaft 20 and fastening means, respectively, and the lower bearing plate 80 is slid onto the shaft 20 and fastening means until the lower bearing plate 80 abuts the lower flange 68. Washers are placed on each fastening means, and the gas release plate 78 is then slid onto the shaft 20 and fastening means until it abuts the washers. The washers establish the fourth space S4 between the lower bearing plate 80 and the gas release plate 78 for escape of gases that accumulate in the pump housing 72. In one embodiment of the invention, the washers are approximately thirty mils in thickness. The gas release plate 78 is temporarily fixed in that position by securing a locking device, such as a nut, to each fastening means and tightening them until the locking device firmly hold the gas release plate in position.

Next the impeller 74 and inducer 76 are attached to the narrow portion 63 of the shaft 20; the keyways 65, 104 are aligned; the key inserted into the cylindrical channel created by the keyways 65, 104; and the impeller 74 and inducer 76 are locked into place. At this point, because the shaft 20 was only loosely coupled to the driveshaft 62, the vertical positioning of the shaft 20 can still be adjusted in the support tube 64. The shaft 20 is adjusted until the third space S3 is established between the impeller disc 98 and the gas release plate 78. In one embodiment, the third space S3 is approximately eight mils. The use of shims can facilitate placement of the impeller 74 relative to the gas release plate 78. When the desired spacing is provided, the shaft 20 is locked into place by firmly securing the clamps on the coupling 117.

After securing the impeller in place, the locking devices that were temporarily holding the gas release plate in place are removed. Finally, the pump housing 72 is placed on the end of the shaft 20 around the inducer 76 and impeller 74. The fastener means are inserted through the through channels 70*a-d*, and the fastening means is securely locked into place so as to join the second end 14 components together. Thus, the pumping device 10 is assembled. The assembled second end 14 can be seen in FIG. 2B. Once final assembly is completed, heating tape can optionally be applied to the alignment canister 42 to help ensure that water does not condense in the interior of the canister, especially in the first bearing 45.

As can be seen in FIG. 1A, during operation, the second end 14 of the device 10 is encapsulated by or otherwise resides within a Dewar container 22 filled with cryogenic liquid. A means for drawing or otherwise removing cryogenic liquid from the Dewar container 22, includes a cryogenic conduit 118 attached to the liquid port 97. An insulated cryogenic transfer hose is a suitable cryogenic conduit. Insulated hoses in general are recommended as the heat load on non-insulated hoses could prevent flow due to a high boiling rate.

When the motor 16 is electrically powered, the driveshaft 62 is rotated, which thereby rotates the shaft 20. Since the shaft 20 and the impeller 74 and inducer 76 are mechanically coupled, the impeller 74 and inducer 74 will also rotate. Rotation of the inducer 76 draws pressurized cryogenic liquid into central region of the impeller 74. The impeller 74 accelerates the fluid outwardly to the perimeter of the impeller disc 98 where it enters the liquid port 97 and travels up the cryogenic conduit 118. The key, described supra, assures that the inducer and impeller rotate at the same angular velocity.

Figure 16:
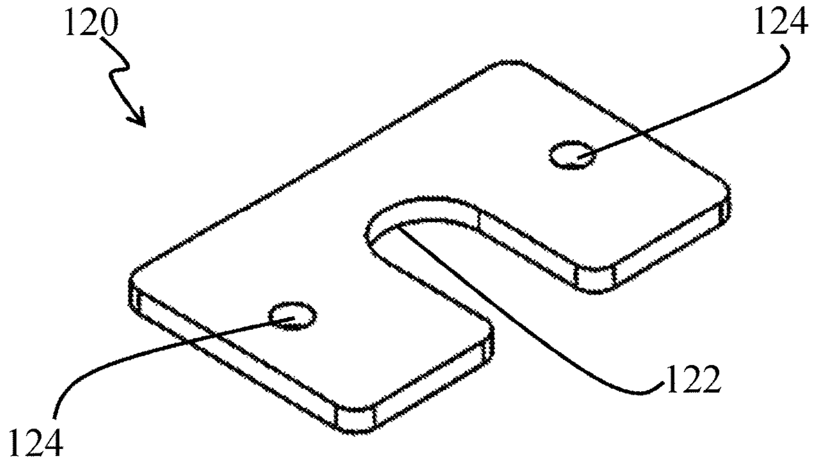
FIG. 16 depicts a lid bracket.

The cryogenic conduit 118 runs through the insulator disc 40 and the lid 24 through the openings 32*a*, 32*b*. On the top surface 24*a* of the lid 24, the conduit 118 is held in place with a lid bracket 120. As shown in FIG. 16, the lid bracket 120 is a flat, rectangular substrate with a notch 122 extending from one side of the substrate into the center of the substrate. Two attachment points 124 are located on each side of the notch 122. The attachment points 124 allow for the lid brackets 120 to be fastened to the recesses 34*a*, 34*b* of the lid 24 and insulator disc 40. The lid brackets 120 keep the conduit from slipping into the cryogenic container, which helps prevent kinks from forming and helps ensure unimpaired flow.

The cryogenic conduit 118 supplies cryogenic liquid to a device, experiment, or other apparatus. After flowing through the device, experiment, or other apparatus, the distal end of the same cryogenic conduit or a second length of cryogenic conduit directs flow back into the Dewar container 22. FIG. 1A shows an outgoing line on the left and a return line entering the Dewar container 22 on the right. In one embodiment of the invention, there are six openings 32*a* in the lid 24. Two of the openings are for entry and exit of the cryogenic conduit. The remaining openings are for visual inspection of the interior of the Dewar container and for ventilation of gases. Ventilation of gases is important to avoid pressure build-up inside the Dewar container, especially during filing.

The presently invented pumping device is capable of providing continuous recirculation of liquid nitrogen for up to six weeks, while operating at 2400 rpms and delivering 2 L/min of liquid nitrogen. Under those parameters, the pump is capable of sustaining a pump head of three meters.

During operation, especially operation over the course of several weeks, some cryogenic liquid will be lost due to evaporation and leaks. In one embodiment of the invention, a level sensor, such as a thermal diode, is placed in the Dewar container. (In this embodiment, the thermal diode turns an electric current on or off, depending on whether it is in contact with liquid nitrogen.) When the liquid drops below a certain level, the sensor triggers an outside reservoir to pump more cryogenic liquid into the Dewar container until the requisite fill level is met. The cryogenic liquid is pumped in through a cryogenic conduit that runs through an opening in the lid. In this embodiment, the lid 24 contains six openings 32*a* with two being for entry and exit of the cryogenic conduit, one for insertion of the level sensor, and one for insertion of the cryogenic conduit from the reserve tank. The remaining two openings are for ventilation and visual inspection.

In another embodiment, the device 10 supplies cryogenic liquid to multiple experiments at one time. The total resistance of the flow in the circuit is the only factor that limits the number of experiments that can be tied to a single pump.

The pump as described was constructed of materials that could withstand cryogenic temperatures. The inventors recommend aluminum 6061 for the components that are submerged in the cryogenic liquid. The support tube, lower flange, and upper flange were made of type 304 stainless steel. The aluminum and stainless steel materials were selected not only for their ability to withstand cryogenic temperatures but also because they experience similar material contractions at cryogenic temperatures. The lid was made from acetal resin, which is a highly crystalline polymer with excellent strength and low temperature properties. Stainless steel bearings, lubricated with graphite were used for the first and second bearings. The bearings are commercially available from Barden Corporation (Danbury, Conn.).

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting, but are instead exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the terms "comprising" and "wherein." Moreover, in the following claims, the terms "first," "second," and "third," are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

The present methods can involve any or all of the steps or conditions discussed above in various combinations, as desired. Accordingly, it will be readily apparent to the skilled artisan that in some of the disclosed methods certain steps can be deleted or additional steps performed without affecting the viability of the methods.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

An exclusive property right or privilege is claimed in the invention as described in the following claims:

1. A cryogenic liquid pump system, said pump system comprising:

a first end having at least an insulating lid and motor;

a second end, wherein the second end is a pump, said pump comprising:

an impeller; and a gas release plate downstream and spaced from the impeller to create a void between the gas release plate and the impeller, wherein the gas release plate has a center defining an aperture;

a shaft disposed between the first end and the second end, wherein the motor imparts mechanical energy to the pump through the shaft, wherein the shaft extends through the aperture in the gas release plate, and wherein the shaft has a smaller diameter than the aperture in the gas plate such that there is an annular void between the gas release plate and the shaft;

a cryogenic liquid container containing a cryogenic liquid, wherein the second end of the pump system is inserted into the cryogenic liquid container and wherein the insulating lid covers the cryogenic liquid container, and wherein the void between the gas release plate and the impeller, the annular void between the impeller and the gas release plate, and the cryogenic fluid container are all in fluid communication;

means for allowing bubbles of the cryogenic liquid in the pump to vent through the gas release plate and into the cryogenic liquid container while confining the cryogenic liquid in the pump system; and at least one cryogenic conduit in fluid communication with the pump, wherein the cryogenic conduit runs from the pump through an opening in the insulating lid to an experimental setup and wherein the cryogenic conduit returns through another opening in the insulating lid.

2. The pump system of claim 1, wherein the pump further comprises an inducer downstream of the impeller, wherein the inducer increases the pressure of the liquid at the impeller.

3. The pump system of claim 1, wherein the impeller is comprised of:

a flat, circular disc; and a plurality of vanes arranged on a surface of the disc.

4. The pump system of claim 3, wherein the plurality of vanes comprises three vanes.

5. The pump system of claim 1, wherein the shaft is substantially enclosed in a support tube.

6. The pump system of claim 1, wherein the cryogenic liquid container contains an amount of cryogenic liquid and wherein the pump system recirculates a substantial portion of the amount of cryogenic liquid as a liquid.

7. The pump system of claim 1, wherein the pump system is capable of operating continuously for a period of at least four weeks.

8. The pump system of claim 6, wherein the pump system is capable of producing a pump head of at least 2 meters.

9. A cryogenic liquid pump system, said pump system comprising:

a first end having at least an insulating lid and motor;

a second end, wherein the second end is a pump, said pump comprising:

an impeller; and a gas release plate downstream of the impeller;

a shaft disposed between the first end and the second end, wherein the motor imparts mechanical energy to the pump through the shaft;

a cryogenic liquid container;

a reservoir of cryogenic liquid;

a level sensor, wherein the second end of the pump system is inserted into the cryogenic liquid container such that the second end pumps liquid from the cryogenic liquid container and wherein the level sensor triggers the reservoir of cryogenic liquid to provide more cryogenic liquid to the container if the amount of cryogenic liquid in the container drops below a certain amount, and wherein the insulating lid covers the cryogenic liquid container; and the pump system further comprises at least one cryogenic conduit in fluid communication with the pump, wherein the cryogenic conduit runs from the pump through an opening in the insulating lid to an experimental setup and wherein the cryogenic conduit returns through another opening in the insulating lid; and means for allowing bubbles of the cryogenic liquid in the pump to vent through the gas release plate and into the reservoir of cryogenic liquid while confining the cryogenic liquid in the pump system.

10. The pump system of claim 9, wherein the cryogenic liquid container contains an amount of cryogenic liquid and wherein the pump system recirculates a substantial portion of the amount of cryogenic liquid as a liquid.

11. The pump system of claim 9, wherein the pump system is capable of operating continuously for a period of at least four weeks.

12. The pump system of claim 9, wherein the pump system is capable of producing a pump head of at least 2 meters.

13. A method for preventing cavitation of a cryogenic liquid in a cryogenic pump system, the method comprising the steps of:

a. constantly maintaining pressure on the liquid in the pump system, wherein maintaining pressure on the liquid further comprises:

i. confining the liquid to the pump system;

ii. subjecting the liquid to an inducer directly below a pump impeller; and iii. expelling the liquid from the cryogenic liquid container, wherein the pump system comprises:

a first end having at least an insulating lid and motor;

a second end, wherein the second end is a pump, said pump comprising:

the impeller; and a gas release plate downstream of the impeller;

a shaft disposed between the first end and the second end, wherein the motor imparts mechanical energy to the pump through the shaft a cryogenic liquid container, wherein the second end of the pump system is inserted into the cryogenic liquid container and wherein the insulating lid covers the cryogenic liquid container; and at least one cryogenic conduit in fluid communication with the pump, wherein the cryogenic conduit runs from the pump through an opening in the insulating lid to an experimental setup and wherein the cryogenic conduit returns through another opening in the insulating lid;

means for allowing bubbles of the cryogenic liquid in the pump to vent through the gas release plate and into the cryogenic liquid container while confining the cryogenic liquid in the pump system; and b. evacuating gas bubbles that form within the pump.

14. The method as recited in claim 13, wherein the step of evacuating gas bubbles that form within the pump is done using the gas release plate.

15. The method as recited in claim 14, wherein a gap is provided between the gas release plate and the impeller.

16. The method as recited in claim 15, wherein the gap is between about 4 and about 10 mils.

17. A cryogenic liquid pump system, said pump system comprising:

a first end having at least an insulating lid and motor;

a second end, wherein the second end is a pump, said pump comprising:

an impeller; and a gas release plate downstream and spaced from the impeller to create a void between the gas release plate and the impeller, wherein the gas release plate has a periphery and a center defining an aperture, and wherein the gas release plate further comprises a plurality of transversely extending apertures formed along the periphery of the gas release plate;

a shaft disposed between the first end and the second end, wherein the motor imparts mechanical energy to the pump through the shaft, wherein the shaft extends through the aperture in the gas release plate, and wherein the shaft has a smaller diameter than the aperture in the gas plate such that there is an annular void between the gas release plate and the shaft;

a cryogenic liquid container, wherein the second end of the pump system is inserted into the cryogenic liquid container and wherein the insulating lid covers the cryogenic liquid container, and wherein the void between the gas release plate and the impeller, the annular void between the impeller and the gas release plate, and the cryogenic fluid container are all in fluid communication; and at least one cryogenic conduit in fluid communication with the pump, wherein the cryogenic conduit runs from the pump through an opening in the insulating lid to an experimental setup and wherein the cryogenic conduit returns through another opening in the insulating lid.

* * * * *